United States Patent [19]

Michel

[11] Patent Number: 5,244,465
[45] Date of Patent: Sep. 14, 1993

[54] REUSABLE INJECTION DEVICE FOR DISTRIBUTING A PRESELECTED DOSE

[75] Inventor: Peter Michel, Burgdorf, Switzerland

[73] Assignee: BYK Gulden Lomberg Chemische Fabrik GmbH, Konstanz, Fed. Rep. of Germany

[21] Appl. No.: 846,766

[22] Filed: Mar. 5, 1992

Related U.S. Application Data

[63] Continuation-in-part of Ser. No. 499,527, Jul. 10, 1990, abandoned.

[30] Foreign Application Priority Data

Oct. 19, 1988 [CH] Switzerland .................. 3892/88

[51] Int. Cl.⁵ .................................................. A61M 5/00
[52] U.S. Cl. ........................................ 604/208; 604/187; 604/218; 604/232
[58] Field of Search ................ 604/207–211, 604/187, 232–234, 220, 228, 218, 131, 134, 135

[56] References Cited

U.S. PATENT DOCUMENTS

| | | | |
|---|---|---|---|
| 4,050,459 | 9/1977 | Sanchez | 604/210 |
| 4,526,294 | 7/1985 | Hirschmann et al. | 604/208 |
| 4,592,745 | 6/1986 | Rex et al. | 604/211 |
| 4,832,694 | 5/1989 | Raphael, III et al. | 604/208 |
| 4,929,238 | 5/1990 | Baum | 604/208 |
| 4,973,318 | 11/1990 | Holm et al. | 604/211 |

FOREIGN PATENT DOCUMENTS

| | | | |
|---|---|---|---|
| 3840000 | 7/1989 | Fed. Rep. of Germany | 604/207 |
| 2561925 | 10/1985 | France | 604/208 |
| 8702895 | 3/1987 | World Int. Prop. O. | |

*Primary Examiner*—C. Fred Rosenbaum
*Assistant Examiner*—Ronald K. Stright, Jr.
*Attorney, Agent, or Firm*—Akoo-Toren

[57] ABSTRACT

A syringe-type injection device for dispensing a preset dose of a liquid drug includes two sleeve-like components releasably connected with each other so as to be aligned in axial direction. One of the sleeve-like components is a holder for a dispensing mechanism and the other of the sleeve-like components is adapted to accommodate an ampoule and a cannula. The dispensing mechanism includes an axially movable piston rod for actuating a plug of the ampoule. The piston rod has a radially projecting cam follower and the holder defines at least one axially extending slot having a predetermined length, wherein the cam follower is received by the at least one slot, such that only a single dose can be dispensed from an ampoule by an axial movement of the piston rod.

13 Claims, 4 Drawing Sheets

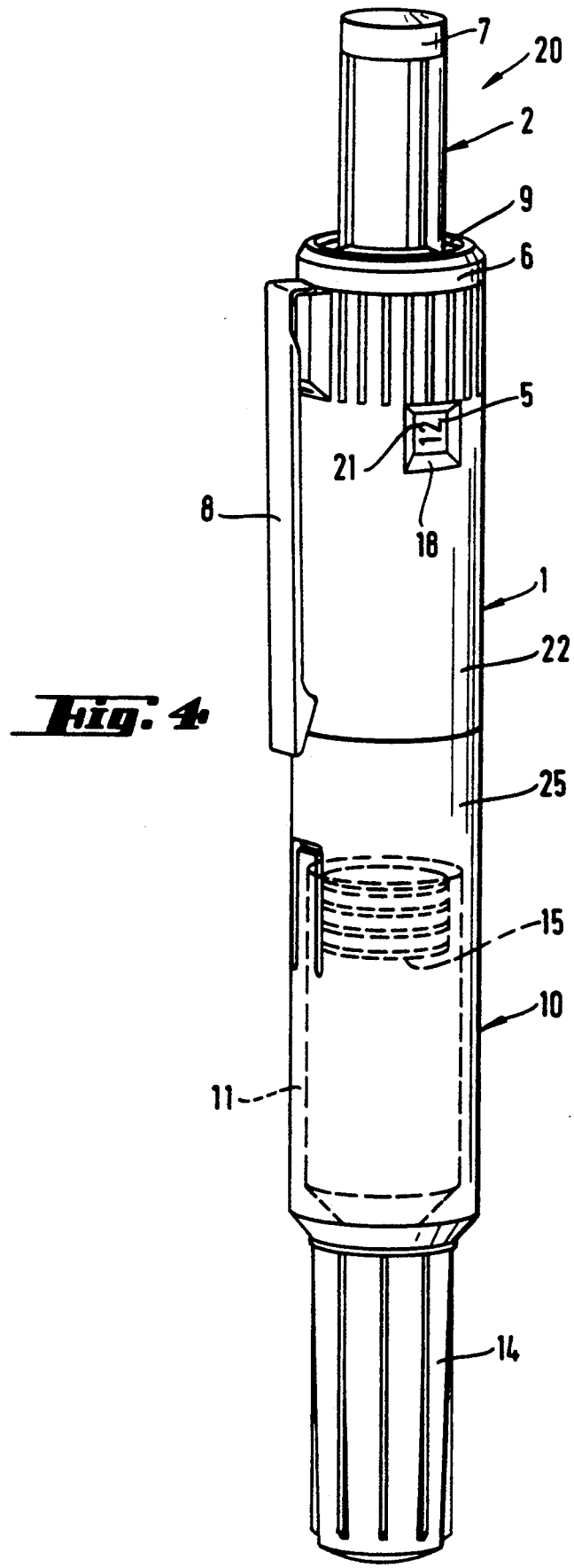

REUSABLE INJECTION DEVICE FOR DISTRIBUTING A PRESELECTED DOSE

This is a continuation-in-part of Ser. No. 07/499,527, filed Jul. 10, 1990, now abandoned.

BACKGROUND OF THE INVENTION

1. Field of the Invention

The invention relates to a syringe device for dispensing a preset dose of a liquid drug.

2. Description of the Prior Art

A syringe device of this type is known from WO 87/02895. This device consists of two sleeve-like housing sections which can be connected together, where the syringe ampoule is screwed into the lower housing section when it is to be used. The drug dose to be dispensed can be preset manually.

The disadvantage of this and other similarly constructed devices in accordance with the state of the art is that they can only be used for drugs for which multishot dispensing from any one ampoule is permissible and usually also desirable.

For the treatment of male erection disorders the drug Papaverin is placed in ampoules without any preservatives, which is why only single-shot dispensing of the drug can be permitted to ensure sterility is maintained.

The dosage varies, depending on the severity of the condition, between 0.25 and 2.0 ml, i.e. if 0.25 ml is dispensed the remaining 1.75 ml is discarded.

This demand pattern cannot, however, be met by conventional dosage aids (PEN syringe devices).

DESCRIPTION OF THE INVENTION

It is the intention of the invention to improve on this situation. The object of the invention is to create a syringe device which can be pre-programmed by the doctor to dispense a fixed single-shot dose which cannot be altered by the patient.

The invention meets the task set by means of a syringe device in which the dispensing system is designed such that only a single dose can be dispensed from any one ampoule.

The advantages offered by the invention lie principally in the fact that, thanks to the syringe device in accordance with the invention, maximum security of operation is guaranteed, since the dispensing of a second dose of the drug, whether intentional or otherwise, is impossible.

A preferred embodiment is characterised therein that the dispensing mechanism comprises a piston rod with a piston rod neck, a dose ring, a retaining spring and a dosing button cap, and the dispensing mechanism is connected by means of a cap with the mechanism holder such that it cannot be disengaged.

In a further embodiment of the syringe device the piston rod consists of an inner hollow cylinder bearing the piston rod neck and, formed integrally with this inner hollow cylinder, of an outer hollow cylinder which has a cam follower on its outer sleeve surface.

A syringe device is particularly preferred in which the interior of the sleeve-like mechanism holder is provided with longitudinal slots of varying length in which a corresponding cam follower of the piston rod can slide. The longitudinal slots are preferably configured equidistantly and preferably with increasing length around the periphery of the inner sleeve of the mechanism holder housing. The ampoule is preferably connected to the ampoule sleeve such that it is difficult to disengage.

A further embodiment of the syringe device is characterized therein that a dose ring is firmly connected radially to the piston rod preferably by means of cam/slot couplings and is provided on its outer periphery with a scale. The housing of the mechanism holder preferably has a window through which the dose ring scale can be viewed from outside.

The housing is advantageously manufactured from an optically opaque material, for example polyamide.

An embodiment of the invention which at the same time serves to explain the operating principle is described in further detail below and is illustrated in the accompanying drawings.

BRIEF DESCRIPTION OF THE DRAWING

FIG. 4 shows a perspective view of the syringe device in accordance with the invention.

DESCRIPTION OF THE PREFERRED EMBODIMENT

Figure 1:
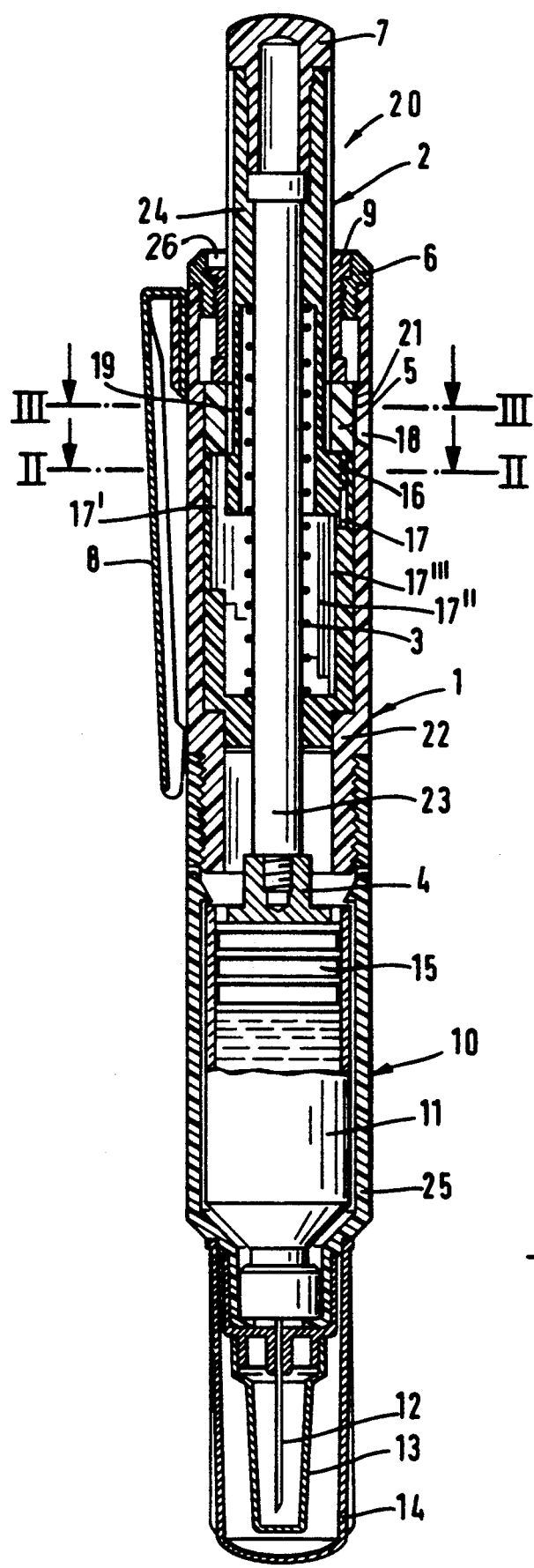
FIG. 1 shows a meridional section through the syringe device according to the invention.
Figure 2:
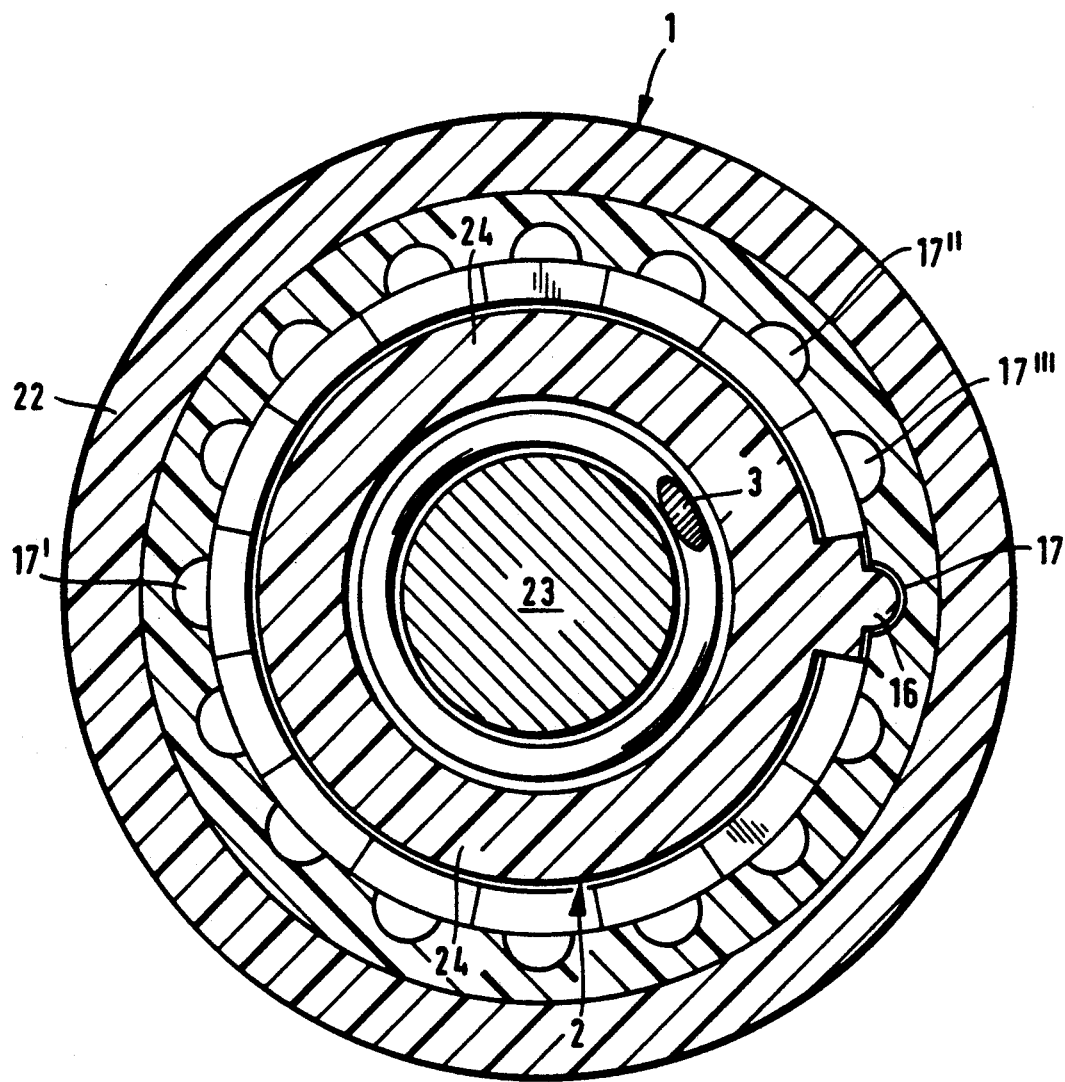
FIG. 2 shows a cross-section along the line II—II in FIG. 1.

The syringe device according to the invention illustrated in longitudinal section in FIG. 1 consists essentially of two sleeve-like components 1, 10 which can be connected together, one of which is designed as the holder 1 for the dispensing mechanism 20 and the other as the ampoule sleeve 10 to accommodate the ampoule 11 and the cannula 12. The assembled syringe device which is held together by the cap 6 can be carried like a fountain pen by means of the clip 8 (FIG. 4). The dispensing mechanism 20 consists of a cylindrical piston rod 2 with an inner hollow cylinder 23 bearing the piston rod neck 4 and, formed integrally with this inner hollow cylinder 23, of an outer hollow cylinder 24 which has a cam follower 16 on its outer sleeve surface (FIG. 2). Externally the dispensing mechanism is designed as a manually operable dosing button 7. When the syringe device is assembled, the dispensing mechanism 20 acts by means of the piston rod neck 4 on the base of the ampoule plug 15 of the drug ampoule 11.

The ampoule sleeve 10 consists of a housing 25 which accommodates the ampoule 11 and can be firmly connected by means of a coupling (not shown) to the housing 22 of the mechanism holder 1. The cannula 12 which connects with the ampoule 11 is protected against damage by means of the inner protective cap 13 and the outer packing sleeve 14.

Figure 3:
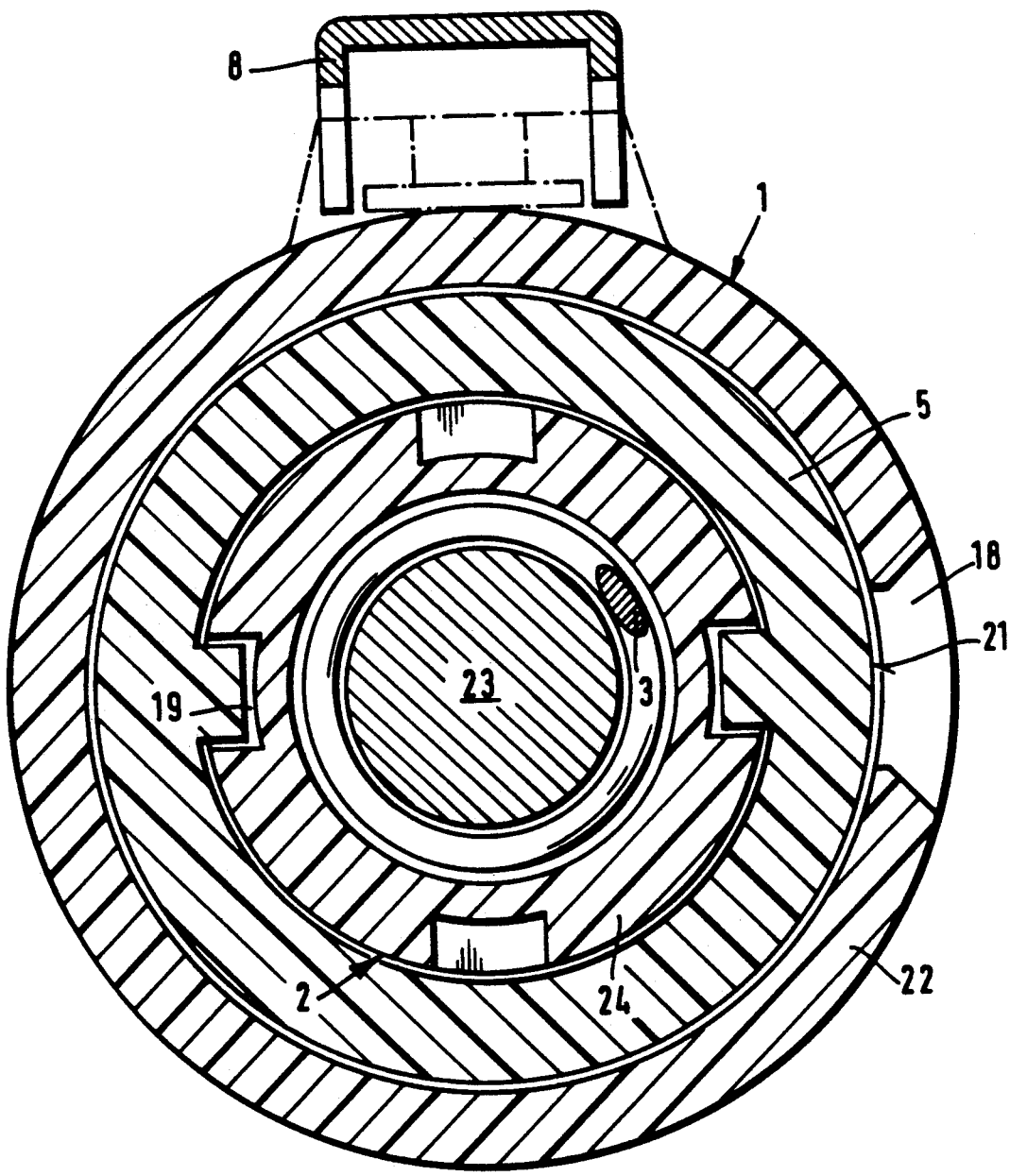
FIG. 3 shows a cross-section along the line III—III in FIG. 1.

The detailed description given below, especially of the dispensing mechanism 20 with reference to the cross-sectional drawings of FIGS. 2 and 3, also serves to describe the operation of the syringe device in accordance with the invention.

A dose ring 5 is firmly mounted radially on the outer hollow cylinder 24 by means of cam/slot couplings 19 such that the ring 5 also turns if the dispensing mechanism 20 is rotated. A scale 21 located on the outer periphery of the dose ring 5 can be read through a window 18 in the housing 22 of the mechanism holder 1 (FIG. 3).

The dispensing mechanism 20 is located such that it can move longitudinally by means of the retaining spring 3 in the mechanism holder 1 which is formed as a hollow cylinder and held in place by the cap 6 which can be screwed onto the housing 22 of the mechanism holder 1. In FIG. 1 the default position of the dispensing mechanism 20 is depicted in which the dose ring 5 lies flush against the screwed-on cap 6 as a result of the force of the retaining spring 3 acting on the dispensing mechanism.

The interior of the housing 22 of the mechanism holder 1 is provided with longitudinal slots 17 of varying length in which the appropriate cam followers 16 of the dispensing mechanism 20 can slide.

The stroke of the dispensing mechanism 20 and thus the drug dose which can be discharged is therefore determined by the length of the longitudinal slot 17 in conjunction with the cam follower 16. If the cam follower 16 slides in a short longitudinal slot 17, as illustrated in FIG. 1, the drug dose is small, whereas if the cam follower 16 slides in a longer longitudinal slot 17''' the drug dose is larger.

The adaptation of the drug dose to the requirements of the patient is performed solely by the doctor who can release the locking ring 9 of the device by means of a special key which engages a recess 26 of locking ring 9 and loosen it until the cam follower 16 of the dispensing mechanism 20 is disengaged from the relevant longitudinal slot 17. The doctor can now select the desired dose by rotating the disengaged dispensing mechanism 20 and re-engaging the cam follower 16 in a shorter or longer longitudinal slot 17. The scale 21 on the dose ring 5 shows the selected setting in the window 18. Once the locking ring 9 is re-tightened by the doctor with the aid of the key the cam follower 16 can only move in a longitudinal direction within the selected longitudinal slot 17. The drug dose to be dispensed is defined solely by the depth of the longitudinal slot 17 working in conjunction with the cam follower 16.

If the syringe device according to the invention is operated as specified no further (second) dose can be dispensed from the ampoule 11 even though there may be a sufficient residual supply of the drug in the ampoule 11. The dispensing mechanism 20 is thus set for single-shot dispensing of a fixed dose and cannot be altered by the patient.

In order to inject a further dose of the drug, the patient must release the ampoule sleeve 10 from the mechanism holder 1 and discard it together with the ampoule 11. The device can only be re-used once a fresh ampoule 11 has been inserted.

So that the patient is not tempted to remove any residual quantity of the drug by some means or other from the ampoule and use it, the housing 25 which accommodates the ampoule 11 is designed such that the ampoule 11 can only be removed from it with extreme difficulty. Furthermore, the housing 25 is preferably made of an optically opaque material, for example polyamide, with the result that any possible residual quantity is not visible.

In order to inject a new dose of the drug, the old lower sleeve-like component 10 is simply replaced by a new one. In this way, the patient is unable to establish whether a residual quantity of drug is left in the ampoule 11 and, if so, how much. This is of particular significance when preservative-free Papaverin is used which, if an overdose were to be taken, would result in irreparable damage.

I claim:

1. A syringe-type injection device including a dispensing mechanism for dispensing a preset dose of liquid drug, comprising:
   first and second sleeve-like components releasably connected to each other so as to be aligned in an axial direction, wherein the first sleeve-like component is a holder for the dispensing mechanism and the second sleeve-like component is an ampoule sleeve having an ampoule and a cannula means for connecting the ampoule with the ampoule sleeve;
   a plug in the ampoule;
   an axially movable piston rod extending from said holder through the dispensing mechanism for actuating the plug of the ampoule, wherein said piston rod has a radially projecting cam follower;
   at least one axially extending slot defined in said holder, wherein said slot has a predetermined length and wherein the cam follower is received by the at least one slot such that only a single dose can be dispensed from the ampoule by an axial movement of the piston rod;
   the piston rod having a piston rod neck for acting on the plug of the ampoule; and
   a cap for connecting the dispensing mechanism with the holder such that it cannot be disengaged.

2. The syringe device according to claim 1, further comprising:
   a dose ring fixedly connected to the piston rod for joint displacement therewith and indicating the present dose of the liquid drug to be dispensed;
   a returning spring supported in the holder by its dispensing mechanism for biasing the piston rod to a first position thereof in which no drug is dispensed; and
   a dosing button cap mounted on an end of the piston rod remote from the ampoule sleeve for moving the piston rod, against the bias of the returning spring, to a second position in which the preset dose of the liquid drug is dispensed.

3. The syringe device according to claim 2, comprising cam and slot couplings connecting the dose ring to the piston rod, wherein the dose ring is provided on the periphery thereof with a scale.

4. The syringe device according to claim 3, wherein the holder has a window, the window being positioned such that the scale of the dose ring can be viewed therethrough.

5. The syringe device according to claim 1, wherein the holder has a plurality of axially extending slots of different lengths.

6. The syringe device according to claim 5, wherein the axially extending slots are spaced from each other uniformly in circumferential direction, and wherein the axially extending slots are arranged with increasing length around the periphery of the holder.

7. The syringe device according to claim 1, wherein the piston rod comprises an inner hollow cylinder bearing the piston rod neck and an outer hollow cylinder surrounding and formed integrally with the inner hollow cylinder, the outer hollow cylinder having an outer sleeve surface, the cam follower being mounted on the outer sleeve surface.

8. A syringe-type injection device including a dispensing mechanism for dispensing a preset dose of a liquid drug, comprising:
   first and second sleeve-like components releasably connected to each other so as to be aligned in an axial direction, wherein the first sleeve-like component is a holder for the dispensing mechanism and the second sleeve-like component is an ampoule sleeve having an ampoule and a cannula means for connecting the ampoule with the ampoule sleeve the ampoule having a plug;

an axially movable piston rod extending from said holder through the dispensing mechanism for actuating the plug of the ampoule;

a radially projecting cam follower on the piston rod;

a plurality of axially extending slots defined on the holder, wherein said slots have different predetermined lengths and wherein the cam follower is received by a respective slot, such that only a respective single preset dose can be dispensed from the ampoule by an axial movement of the piston rod.

9. The syringe device according to claim 8, wherein the component accommodating the ampoule includes a housing, the housing being a single-piece component.

10. The syringe device according to claim 9, wherein the housing is of an optically opaque material.

11. The syringe device according to claim 10, wherein the opaque material is a polyamide.

12. The syringe device according to claim 8, wherein the ampoule is tightly connected to the ampoule sleeve such that it is difficult to disengage.

13. The syringe device according to claim 8, further comprising adjustable locking means for defining a position of the piston rod in which the cam follower is received in the respective slot.

* * * * *